US007015322B1

(12) United States Patent
Eckardt et al.

(10) Patent No.: US 7,015,322 B1
(45) Date of Patent: Mar. 21, 2006

(54) PROCESS FOR PRODUCING CARBAMAZEPINE

(75) Inventors: Rudolf Eckardt, Radebeul (DE); Hans-Joachim Jänsch, Radebeul (DE)

(73) Assignee: Degussa AG, Hanau-Wolfgang (DE)

( * ) Notice: Subject to any disclaimer, the term of this patent is extended or adjusted under 35 U.S.C. 154(b) by 0 days.

(21) Appl. No.: 09/447,490

(22) Filed: Nov. 23, 1999

Related U.S. Application Data

(63) Continuation of application No. 08/275,025, filed on Jul. 14, 1994, now abandoned.

(51) Int. Cl.
*C07D 223/26* (2006.01)
(52) U.S. Cl. ..................................... 540/589
(58) Field of Classification Search ............... 540/589
See application file for complete search history.

(56) References Cited

FOREIGN PATENT DOCUMENTS

EP         277095    *  3/1988

OTHER PUBLICATIONS

BPAI Decision in Appeal # 95-4841.*

Austin Patterson, "A German-English Dictionary for Chemists", 3rd Ed., Wiley, New York.*
"Handbook of Chemistry and Physics, 42nd Edition", Charles D. Hodgman Editor, The Chemical Rubber Publishing Co., Cleveland, OH, 1962, p 1753-1754.*
Gmelins Handbuch der anorganischen Chemie, Kohlenstoff, Teil D 1, Dieter Koschel, Editor, Verlag Chemie, Weinheim, 1971, p 344.*
Lowry and Richardson, Mechanism and Theory in Organic Chemistry, 3rd Edition, Harper and Row, New York, 1987, p 199.*
Ruff, F. and Csizmadia, I.G. "Organic Reactions, Equilibria, Kinetics, and Mechanism", Elsevier, New York, 1994, p. 60.*
"Statement (Report) of Inspection/Quality Control", Koytcheff, John M., Jul. 14, 2000.*
Acklin (EP 277,095) translation, "Statement (Report) of Inspection/Quality Control", Koytcheff, John M., Jul. 14, 2000.*

* cited by examiner

*Primary Examiner*—Thomas C. McKenzie
(74) *Attorney, Agent, or Firm*—Goodwin Procter, LLP

(57) ABSTRACT

The invention concerns a process for producing 5H-dibenz [b,f]azepine-5-carboxamide (carbamazepine) by reacting iminostilbene with an alkali cyanate in acetic acid or a mixture of acetic acid with water or with alcohol.

18 Claims, No Drawings

PROCESS FOR PRODUCING CARBAMAZEPINE

This is a continuation of application Ser. No. 08/275,025, filed on Jul. 14, 1994, now abandoned.

FIELD OF THE INVENTION

The present invention is a process for producing 5H-dibenz[b,f]azepine-5-carboxamide, also known by the generic name carbamazepine.

BACKGROUND OF THE INVENTION

Carbamazepine has the formula

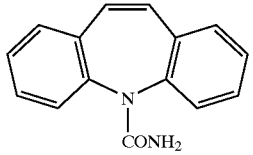

and is a valuable agent for treating the central nervous system, such as an anticonvulsant, or to produce analgesia.

Processes for producing carbamazepine are known for example from U.S. Pat. No. 2,948,718, European patent No. 423,679, and German (East) patent Nos. 297,962 and 298,508, which disclose reacting iminostilbene with phosgene to produce 5H-dibenz[b,f]azepine-5-carboxylic acid chloride, followed by the addition of ammonia.

From British patent No. 1,246,606 it is known to produce carbamazepine 10,11-dihydro-5H-dibenz[b,f]azepine seriatim with phosgene, 1,3-dibromo-5,5-dimethyl-hydan-toin, then potassium carbonate, and ammonia.

Another method for the production of carbamazepine is known from German published patent application No. 2,307,174 by the reaction of iminostilbene with an acylisocyanate to produce 5H-dibenz[b,f]azepin-5-(N-acyl)-carboxamide followed by hydrolysis. German published patent application No. 2,637,666 discloses the reaction of 5-(methylisothiocarbamoyl)-5H-dibenz[b,f]azepine-hydroiodide with a base.

European patent No. 29,409 discloses the acid or alkaline hydrolysis of 5-cyano-5H-dibenz[b,f]azepine.

All of the aforementioned known processes have a variety of drawbacks. For example, many known processes require the use of the highly toxic phosgene or halogen cyanide. In the process according to German published patent application No. 2,307,174 the use of unstable and generally unavailable acylisocyanates is required. In the process of German published patent application No. 2,637,666 toxic methylmercaptan is a byproduct.

Carbamazepine can be, furthermore, also produced by reaction of iminostilbene with hydrogen cyanide in an organic solvent or solvent mixture in the presence of an acidifier as described in European patent No. 277,095. The acidifier has only a catalytic role and increases the conversion rate of the iminostilbene and the cyan-hydroxide. The latter is introduced into the reaction mixture as a gas, but can also be recovered by reacting a cyanide salt with an acid.

Since the hydrogen cyanide enters into undesired side reactions with water, alcohols, and amines, the reaction is to be carried out under strongly aprotic conditions in solutions which are substantially free of water, alcohol and amines, and without the use of water vapors. Such conditions make the entire process very difficult and require additional materials and special procedures.

DESCRIPTION OF THE INVENTION

The present invention provides a technically simple method for producing carbamazepine which is free of the aforementioned drawbacks.

In accordance with the present invention it has been unexpectedly found that carbamazepine can be simply produced, without any attendant dangers and difficulties by reacting iminostilbene with alkali cyanates in aqueous or alcoholic acetic acid mixtures. The reaction of the iminostilbene can be carried out with an alkali cyanate, such as sodium or potassium cyanate, suitably within a temperature range of from about 20° C. to about 100° C.

When an aqueous acetic acid mixture is used, suitably up to about 20% by weight water based on the mixture is used with the acetic acid. In alcoholic acetic acid mixtures suitably up to about 10% alcohol can be used in the mixture. Suitably methanol and ethanol can be used as the alcohols.

In accordance with a suitable embodiment of the present invention the alkali cyanate is stirred at about 60° C. to a suspension of iminostilbene in an acetic acid mixture by using an about 50 mole % access of the cyanate related to the amount of the iminostilbene.

The alkali cyanate can be gradually added in installments of the solid material. Suitably, however, an aqueous solution of the alkali cyanate is added dropwise, especially when the highly water soluble potassium cyanate is used. The dropwise 10=addition to the alkali cyanate provides a particularly suitable, easy way of carrying out the process of the present invention.

The solution mixture employed for the reaction of iminostilbene with the alkali cyanate, can be subsequently distilled off from the reaction mixture and reused in the process.

The successful employment of the process of the present invention is surprising from a number of points of view. It is known from the literature that a number of aromatic primary amines can be converted to the corresponding urea derivatives with an alkali cyanate in aqueous acetic acid solutions, wherein, for example, Kurzer disclosed the use in Org. Synth. Coll. Vol. IV, p. 49 the use of 1:10 to 1:1 acetic acid water mixtures. However, under these reactions conditions the iminostilbene, a secondary diarylamine will not react with alkali cyanates. This is partly because iminostilbene is much less basic compared to the aforementioned aromatic primary amines, and partly because iminostilbene is much less soluble in acetic acid than those amines. This low solubility becomes even lower when water or alcohol are added.

On the basis of the statements in European patent No. 277,095 a person skilled in the art would conclude that even traces of water, such as those contained in air, would detrimentally affect the reaction.

Therefore, it was entirely unpredictable that the conversion of iminostilbene with an alklali cyanate in acetic acid mixtures with about up to 20 wt. % water, can be easily carried out with an excellent yield. Similarly, the high yields of the present invention obtained by the reaction in alcoholic acetic acid mixtures was also surprising. It was also entirely unexpected that very substantially improved yields can be obtained with the process of the present invention with acetic acid mixtures containing as little as from about 5% to about 10% wt. water or alcohol.

The following examples further illustrate the present invention.

EXAMPLE 1

A stirred suspension of 100 g iminostilbene in 1000 ml acetic acid is heated to 60° C. Next, within 160 minutes 54 g 90% sodium cyanate is added in 11 installments. During the reaction the iminostilbene goes almost completely into solution before carbamazepine begins to crystalize out. After the addition of the sodium cyanate is completed the reaction mixture is continued to be stirred for another 20 minutes at 60° C. Then it is cooled to 18° C.–20° C. and stirred at that temperature for two more hours. The precipitated carbamazepine is collected by filtration, washed with 60 ml water free acetic acid, and is dried. A yield of 107.8 g (87.9% of theoretical) of carbamazepine is obtained having a melting point of 193° C. to 194° C.

The acetic acid is distilled off from the mother liquor under vacuum produced by a water jet aspirator. The sodium acetate is dissolved from the residue with water, the carbamazepine is collected, dried, and recrystallized from toluene. A further 9.8 g (8.0% of theoretical) carbamazepine is obtained having a melting point of 191° C. to 193° C. Thus, the gross yield is 95.9% of theoretical.

EXAMPLE 2

A suspension of 100 g iminostilbene in a mixture of 900 ml water-free acetic acid and 100 ml water is heated to 60° C. during stirring, then within 2.75 hours 58.3 g of 90% sodium cyanate is added in 16 installments. After a two hour reaction time the mass is heated briefly to 80° C. to bring small amounts of undissolved iminostilbene into solution.

After the adding of the sodium cyanate is completed, the reaction mixture is cooled to 18° C. to 20° C. and stirred for half and hour at this temperature. The precipitated carbamazepine is sucked off, washed with 70 ml of a mixture of 63 ml acetic acid and 9 ml water, and is then dried. 110.1 g of the end product is obtained (89.8% of theoretical), having a melting point of 191° C. to 195° C.

The solvent is distilled off from the mother liquor and the sodium acetate is dissolved from the residue, carbamazepine is sucked off, dried, and recrystallized from toluene to produce a further 5 g (4.1%) carbamazepine, having a melting point of 188° C. to 190° C., resulting in a total yield of 93.9%.

EXAMPLE 3

A suspension of 30 g iminostilbene in admixture with 225 ml acetic acid and 45 ml water is heated to 60° C. while stirring. Then within 2.75 hours, 17.5 g 90% sodium cyanate is added in 16 installments. After 1.5 hours reaction time the mixture is briefly heated to 80° C. to dissolve any undissolved iminostilbene. After the addition of the sodium cyanate the reaction mixture is rested for further ten minutes at 60° C. and then cooled to 18° C. to 20° C. and stirred for a further hour at this temperature. The precipitated carbamazepine is sucked off and washed in 20 ml acetic acid water mixture (6:1) and then dried. 32.9 g (89.2% of theoretical) of the end product is obtained, having a melting point of 189° C. to 191° C.

The entire solvent is distilled off from the mother liquor and the sodium acetate is dissolved from the residue with water, carbamazepine is sucked off, dried and recrystallized from toluene. Thus a further 1.8 g (4.8%) carbamazepine is obtained having a melting point of 191° C. to 193° C., producing a total yield of 94%.

EXAMPLE 4

A suspension of 60 g iminostilbene in 600 ml acetic acid is heated during stirring to 60° C. Next a solution of 40 g 98% potassium cyanate in 66 ml water is added dropwise for 2 hours, while the reaction mixture is briefly heated to 80° C. to bring all of the iminostilbene into solution. After the addition of the potassium cyanate, the reaction mixture is cooled to room temperature and the precipitating carbamazepine is sucked off and dried. 33 g (89.9% of theoretical), having a melting point of 190–193° C. are obtained.

The mother liquor is further processed as described in Example 3, to yield a further 3.3 g of the end product, resulting in a total yield of 93.2% of the theoretical.

EXAMPLE 5

A stirred suspension of 100 g iminostilbene in a mixture of 1000 ml acetic acid and 150 ml water is heated to 60° C. Then within 5 hours 60.8 g 98% potassium cyanate is added in 13 installments. After the potassium cyanate addition is complete the reaction mixture is stirred for a further 30 minutes and cooled to 18° C. to 20° C. The precipitated crystals are sucked off, washed with a mixture of 60 ml acetic acid and 400 ml water, and then dried, yielding 11.2 g end product (90.9% of theoretical), having a melting point of 191° C. to 193° C.

The solvent is distilled off from the mother liquor and potassium acetate is dissolved from the residue. The carbamazepine is sucked off, washed with water, recrystallized from toluene, to yield a further 7.5 g (6.1% of theoretical) carbamazepine, having a melting point of 190° C. to 192° C. The total yield is 97%.

EXAMPLE 6

3 kg iminostilbene are stirred in a mixture of 28.5 l acetic acid and 1.5 l water, and heated to 60° C. Within about 2 hours 1.66 kg 98% sodium cyanate is added, the the mixture is cooled to 15° C. and held for a further 2 hours between 15° C. to 20° C., then the crystals are sucked off, washed with 2 l acetic acid and dried, yielding 3.39 kg (92.5% of theoretical) of the end product, having a melting point of 190° C. to 192° C.

Next 22 l acetic acid was distilled off, 10 l water was added to the residue, briefly stirred, sucked off and washed with 5 l water and dried and a further 0.28 kg of the product was obtained which was recrystallized from toluene to 0.23 kg (6.3% of theoretical) having a melting point of 191° C. to 194° C. This resulted in a total yield of 98.8% of theoretical).

EXAMPLE 7

30 g iminostilbene are heated to 60° C. in 360 ml acetic acid and 50 ml ethanol, and 20 g 98% sodium cyanate is added within 1.5 hours at this temperature. After a short heating to 80° C., the mixture is further stirred at 60° C., and then cooled to 15° C., sucked off, washed with 20 l acetic acid and dried to yield 29.4 g (80.3% of theoretical) of carbamazepine, having a melting point of 189° C. to 192° C.

After adding 1 g sodium cyanate to the mother liquor, distilling it, adding water to the residue and recrystallization of the dried product from toluene a further 4.9 g (13.4% of theoretical) carbamazepine is obtained with a melting point of 190° C. to 193° C. to result in a total yield of 93.7%.

We claim:

1. A process for producing carbamazepine, which comprises reacting iminostilbene with an alkali cyanate in an aqueous acetic acid solution or an alcoholic acetic acid solution, and recovering the resulting carbamazepine, wherein the aqueous acetic acid solution contains about 5% to about 20% water.

2. The process of claim 1 wherein iminostilbene reacts with the alkali cyanate in the absence of a strong acid.

3. The process of claim 1 wherein the alcoholic acetic acid solution contains up to about 10% alcohol.

4. A process for producing carbamazepine, comprising the steps of:
   reacting iminostilbene with an alkali cyanate in an aqueous acetic acid mixture, wherein said aqueous acetic acid mixture comprises acetic acid and about 5% to about 20% by weight of water; and
   recovering the resulting carbamazepine.

5. The process of claim 4, wherein said aqueous acetic acid mixture contains from about 5% to about 10% by weight of water.

6. The process of claim 4, wherein said alkali cyanate is sodium cyanate or potassium cyanate.

7. The process of claim 4, wherein said reacting step is carried out within a temperature range of from about 20° C. to about 100° C.

8. The process of claim 4, wherein in said reacting step, said alkali cyanate is gradually added to a suspension of iminostilbene in said aqueous acetic acid mixture.

9. The process of claim 8, wherein said alkali cyanate is added as a solid material.

10. The process of claim 8, wherein said alkali cyanate is added in the form of an aqueous solution.

11. A process for producing carbamazepine, comprising the steps of:
    reacting iminostilbene with an alkali cyanate in an alcoholic acetic acid mixture; and
    recovering the resulting carbamazepine.

12. The process of claim 11, wherein said alcoholic acetic acid mixture contains up to about 10% by weight of alcohol.

13. The process of claim 12, wherein said alcohol is methanol or ethanol.

14. The process of claim 11, wherein said alkali cyanate is sodium cyanate or potassium cyanate.

15. The process of claim 11, wherein said reacting step is carried out within a temperature range of from about 20° C. to about 100° C.

16. The process of claim 11, wherein in said reacting step, said alkali cyanate is gradually added to a suspension of iminostilbene in said alcoholic acetic acid mixture.

17. The process of claim 16, wherein said alkali cyanate is added as a solid material.

18. The process of claim 16, wherein said alkali cyanate is added in the form of an aqueous solution.

* * * * *